United States Patent [19]

Sherwin et al.

[11] Patent Number: 4,560,653

[45] Date of Patent: Dec. 24, 1985

[54] PROCESS FOR PREPARING L-ASPARTIC ACID

[75] Inventors: Martin B. Sherwin, Potomac; John J. Blouin, Catonsville, both of Md.

[73] Assignee: W. R. Grace & Co., New York, N.Y.

[21] Appl. No.: 501,421

[22] Filed: Jun. 6, 1983

[51] Int. Cl.$^4$ .............................................. C12P 13/20
[52] U.S. Cl. ................................................... 435/109
[58] Field of Search ......................................... 435/109

[56] References Cited

U.S. PATENT DOCUMENTS

| | | |
|---|---|---|
| 2,816,923 | 12/1957 | Stephenson et al. |
| 2,927,059 | 3/1960 | Good et al. |
| 2,955,136 | 10/1960 | Sullivan et al. |
| 2,971,890 | 3/1961 | Ogawa et al. |
| 3,183,170 | 5/1965 | Kitai et al. |
| 3,198,712 | 8/1965 | Takahashi et al. |
| 3,214,345 | 10/1965 | Chibata et al. |
| 3,222,258 | 12/1965 | Iizuka et al. |
| 3,310,475 | 3/1967 | Yamatodani et al. ............ 195/30 |
| 3,332,992 | 7/1967 | Brown et al. ..................... 260/537 |
| 3,391,059 | 7/1968 | Takamura et al. |
| 3,649,457 | 3/1972 | Westman |
| 3,672,955 | 6/1972 | Stanley |
| 3,705,084 | 12/1972 | Reynolds |
| 3,788,948 | 1/1974 | Kagedal et al. |
| 3,791,926 | 2/1974 | Chibata et al. |
| 3,791,927 | 2/1974 | Forgione et al. |
| 3,905,923 | 9/1975 | Klug |
| 3,907,641 | 9/1975 | Nakayama et al. |
| 3,928,138 | 12/1975 | Wood et al. |
| 3,929,574 | 12/1975 | Wood et al. |
| 3,933,586 | 1/1976 | Duc |
| 3,975,350 | 8/1976 | Hudgin et al. |
| 4,000,040 | 12/1976 | Tsuchuda et al. |
| 4,013,508 | 3/1977 | Zangrandi et al. ............... 195/28 |
| 4,048,018 | 9/1977 | Coughlin et al. |
| 4,312,946 | 1/1982 | Wood et al. ..................... 435/182 |
| 4,456,685 | 6/1984 | Guthrie ............................ 435/109 |

FOREIGN PATENT DOCUMENTS

| | | |
|---|---|---|
| 684057 | 4/1964 | Canada . |
| 697310 | 11/1964 | Canada . |
| 0138383 | 8/1982 | Japan ................................ 435/109 |
| 880234 | 10/1961 | United Kingdom . |
| 953414 | 3/1964 | United Kingdom . |
| 659611 | 3/1977 | U.S.S.R. . |
| 644833 | 1/1979 | U.S.S.R. . |

OTHER PUBLICATIONS

Royals—Advanced Organic Chemistry—348-5-9—1954.
Chibata et al.,—Applied Microbiology—27/878-8-5—1974.
Kisumi et al.,—Chemical Abstracts—54/25547—1960 Article.
Sato—Biochemica et Biophysica Acta—570/179-8-6—1979.
Sonomoto et al.,—Agric. Biol. Chem.—44/1119-2-6—1980.
Chemical Abstracts I: 97:53996p.
Chemical Abstracts II: 94:63756n.

Primary Examiner—Sam Rosen
Assistant Examiner—L. Krawczewicz
Attorney, Agent, or Firm—Jill H. Krafte

[57] ABSTRACT

A process for preparing L-aspartic acid by contacting fumarate ion-containing solution with aspartase or aspartase-producing microorganisms, adding maleic acid to insolubilize or precipitate the L-aspartic acid, isomerizing maleic acid in the supernatant liquid to form fumaric acid and recycling the fumaric acid into contact with the enzyme or microorganisms.

7 Claims, 1 Drawing Figure

PROCESS FOR PREPARING L-ASPARTIC ACID

CROSS REFERENCES TO RELATED APPLICATIONS

The following applications relate to and are copending with the present application: Ser. No. 452,467, by Swann et al., filed Dec. 23, 1982, describes a process for converting fumaric acid to L-aspartic acid using aspartase-producing microorganisms immobilized in a polyurethane carrier. Ser. No. 452,579, by Swann et al., filed Dec. 23, 1982, describes the process for producing L-amino acids using microorganisms immobilized in a polyurethane carrier.

BACKGROUND OF THE INVENTION

It is well known that aspartase has the ability to convert ammonium fumarate into L-aspartate. Various methods for producing L-aspartate by the enzymatic reaction of aspartase with ammonium fumarate are known. For example, L-aspartic acid can be prepared by cultivating an aspartase-producing microorganism in a nutrient medium containing fumaric acid or fumarate ion. U.S. Pat. No. 3,214,345 discloses the use of *E. coli* cells to produce L-aspartic acid from ammonium fumarate. Alternatively, L-aspartic acid can be prepared either by reacting resting whole cells containing aspartase with ammonium fumarate or by extracting the enzyme and heating the same with ammonium fumarate. However, these methods are disadvantageous because the resulting L-aspartic acid is contaminated with the enzyme, the microbial cells, nutrient sources, etc. Accordingly, in order to recover L-aspartic acid having high purity, additional steps for removing the enzyme and other contaminants are required. Frequently these methods destroy the enzyme and/or the microorganism so that they can be used only once.

To overcome the above disadvantages, it has been suggested to immobilize the enzyme or enzyme-producing microorganism in or on a support structure. For example, methods of binding or immobilizing enzymes are disclosed in Japanese Patent Publication No. 6870/1970 (binding to anion exchange polysaccharide adsorbent), U.S. Pat. No. 3,672,955 to Stanley (enzymes bound to polyurethane), U.S. Pat. No. 3,975,350 to Hudgin et al. (enzymes entrapped in hydrophilic polymer), and U.S. Pat. Nos. 4,312,946; 3,929,574; or 3,928,138 to Wood et al. (enzymes immobilized in polyurethane foams). Similarly methods of binding or immobilizing microorganisms are disclosed in Japanese Patent Publication No. 17,587/1970 (encapsulated in polyacrylates as polymeric carriers), Russian Patent Publications Nos. SU 423,976 and SU 451,483 (immobilization of *E. coli* in polyacrylamide cells), a journal article by Sato, *Biochemica et Biophysica Acta*, 570,179–186 (1979) (carrageenan as carrier polymer) and pending U.S. patent application Ser. No. 452,579 (Swann et al.), filed Dec. 23, 1982 (immobilized in a polyurethane carrier).

In addition to the preceding references, U.S. Pat. No. 3,391,059 describes a process wherein microorganisms capable of converting maleic acid directly into L-aspartic acid are isolated. In such microorganisms, maleic and/or malonic acid induces formation of enzymes used in the conversion of maleic acid to L-aspartic acid. U.S. Pat. No. 4,013,508 describes conversion of hydrocarbons into L-aspartic acid utilizing two different microorganisms. The first converts hydrocarbons to fumaric acid and the second converts fumaric acid to L-aspartic acid. Maleic acid is produced as a by-product.

Methods for isomerizing maleic acid to fumaric acid are well known. U.S. Pat. No. 2,816,923 describes an isomerization process wherein the maleic acid is heated. It is indicated that isomerization using hydrochloric acid is too expensive and the combination of a halogen (e.g., bromine) plus ultraviolet light is not effective. U.S. Pat. No. 2,955,136 utilizes nitric acid plus a catalyst such as bromine, iodine, hydrochloric acid, hydrobromic acid, potassium thiocyanate or sodium bromide. U.S. Pat. No. 3,332,992 accomplishes the isomerization by use of a bromine-providing catalyst and an oxidizing agent. A suitable oxidizing agent is ammonium persulphate and the bromine-providing catalyst can be ammonium bromide.

DESCRIPTION OF THE INVENTION

Figure 1:
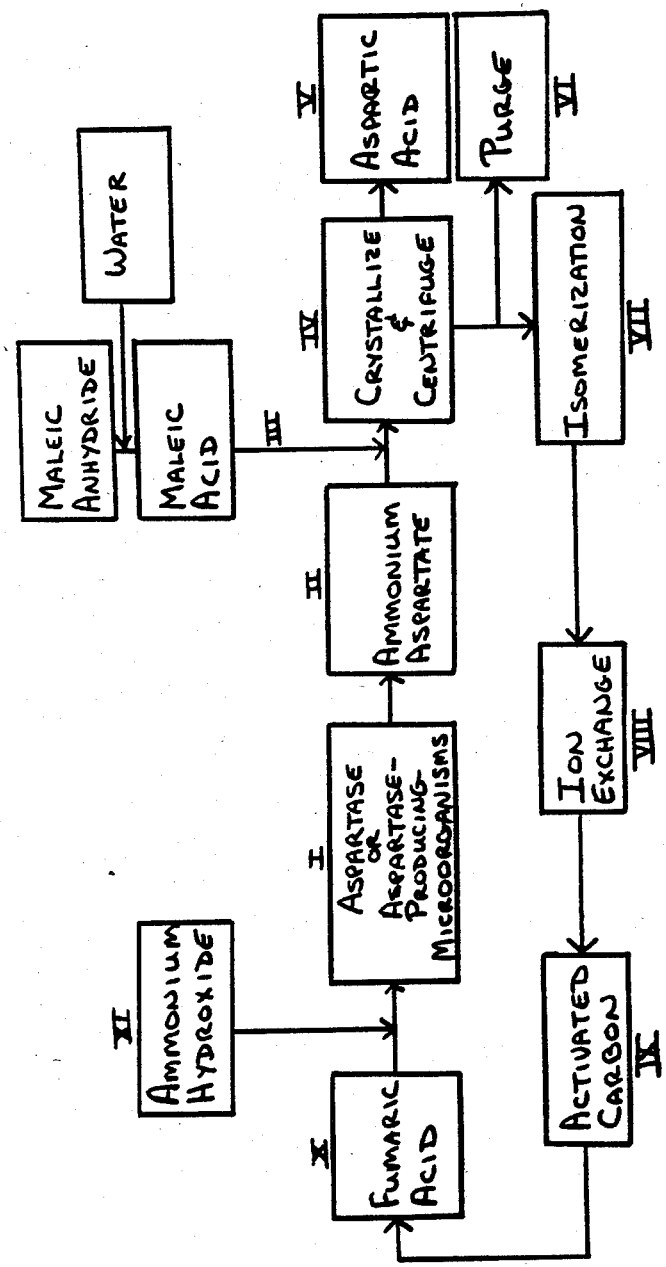
FIG. 1 is a flow diagram of one embodiment of the process of this invention.

The invention is an improved process for preparing L-aspartic acid wherein a substrate comprising fumarate ion and other ingredients (as described below) is contacted with aspartase enzyme or aspartase-producing microorganisms, preferably immobilized in an inert carrier. Enzymes produced by the microorganisms convert fumaric acid to L-aspartic acid (or fumarate ion to L-aspartate, from which L-aspartic acid is formed). L-aspartic acid then is removed from solution (i.e., isolated) by reducing the pH to less than about 5.3 and preferably from about 4 to 3. In prior art processes, the pH is reduced by addition of mineral acids such as sulfuric acid.

The improvement of the present invention, however, provides for reduction of pH by addition of maleic anhydride, maleic acid or salts thereof. L-aspartic acid precipitates from solution and is isolated and further processed, e.g., by water washing. The maleic acid in the supernatant liquid is then isomerized to form fumaric acid and the pH is adjusted to about 8 to 9. This fumaric acid solution then is passed into contact with the enzyme or microorganisms to again convert fumaric acid into L-aspartic acid.

As employed in this invention the terms "L-aspartic acid" and "aspartic acid" are used interchangeably. In addition, "aspartate" and "aspartic acid" may be used synonymously herein. The term "maleic acid" is intended to include maleic anhydride as well as suitable water-soluble salts of maleic acid, for example quarternary ammonium salts or alkaline metal salts such as sodium or potassium malate.

In the prior art, precipitation of L-aspartic acid was accomplished by lowering the pH with sulfuric acid or other mineral acids which introduce ammonium sulphate or other by-product materials. These materials represent impurities to be removed from the L-aspartic acid product or alternatively to be disposed of as wastestreams. Thus, for economical and ecological reasons it is preferable to have a closed system wherein the supernatant liquid, following precipitation of L-aspartic acid, is recirculated.

The present invention utilizes maleic acid to lower the pH to cause aspartic acid precipitation, thereby avoiding introduction of impurities and attendant waste disposal problem. The recirculation objective is accomplished by converting the maleic acid to fumaric acid which can then be recycled. Rather than introducing undesirable by-products, the maleic acid (following isomerization) serves as a source of L-aspartic acid and also permits the process to be conducted as a "closed loop." An additional advantage is that the maleic acid is presently a less expensive raw material than fumaric acid. It also has been found that the presence of maleic acid does not appear to interfere with the microbial enzymatic reactions converting fumaric acid to L-aspartic acid.

L-aspartic acid can be prepared by contacting aspartase, aspartase-producing microorganisms, carrier-bound aspartase or carrier-bound aspartase-producing microorganisms with fumarate ion. For the sake of simplicity, the following discussion will refer to immobilized microorganisms, but this will be understood to encompass bound or unbound aspartase and unbound microorganisms as well.

With reference now to the flow diagram of FIG. 1, the first step of the preferred embodiment of this process (step I in FIG. 1) is contacting the microorganisms and/or enzyme with fumaric acid. The fumaric acid solution contacted with the microorganisms possesses a pH of about 8 to about 9.3 and preferably about 8.3 to 9.1. The pH is adjusted with ammonium hydroxide (step XI). The temperature is from about 10° C. to 50° C. and preferably about 20° C. to 45° C. The fumaric acid concentration is about 0.4 to 1.6 molar and the total concentration of carboxylic acid anions (i.e., fumaric and maleic combined) is from about 0.5 to 2.5 molar. The presence of maleic acid anions results because isomerization of maleic to fumaric acid is generally incomplete. Also, a small amount of L-aspartic acid (e.g., less than about 0.05 molar) is generally present. Ammonium aspartate is produced from the enzyme reaction of aspartase and fumaric acid in the presence of ammonium ions (step II).

As discussed above, following contact with the microorganisms or enzyme, the pH of the solution is lowered to less than about 5.3 and preferably from about 4 to 3 by addition of maleic acid (step III). The addition of the maleic acid serves simultaneously to reduce the pH and replenish the supply of organic acid lost by the simultaneous precipitation of L-aspartic acid. Generally, within the pH range of from 3.5 to about 3, from about 70 to 97 molar % of the L-aspartic acid precipitates. Accordingly, the maleic/aspartic acid molar ratio during the precipitation step (and including all material in both the liquid and solid phases) is about 1.

To optimize crystal formation in the precipitation step, it is preferable to heat the aspartic acid solution to about 60° C. and allow the solution to cool to about 25° C. Crystals are formed as the solution cools (step IV). Centrifugation (step IV) allows the solid crystals of aspartic acid to be separated from the liquid supernatant (step V). At this point, part of the supernatant may be purged from the system if desired (step VI).

Following removal of the L-aspartic acid, the supernatant generally possesses relatively large amounts of maleic acid and residual amounts of L-aspartic acid. The maleic acid content of the supernatant phase is isomerized to fumaric acid by contact with a conventional isomerization catalyst (step VII). A wide variety of such catalysts are known. However, it is preferred to use a catalyst employing a water-soluble bromine-providing compound and an oxidizing agent.

Water-soluble bromine-providing compounds are described at column 2, lines 12–56 of U.S. Pat. No. 3,332,992. Oxidizing agents are described at column 2, lines 67, through column 3, line 9, of U.S. Pat. No. 3,332,991. All portions of U.S. Pat. No. 3,332,992 referred to above are incorporated herein by reference. The mole ratio of bromine-providing compound to maleic acid in the supernatant phase is from 0.01 to 0.3, preferably 0.02 to 0.18, and the molar ratio of oxidizing agent to maleic acid is from 0.003 to 0.1, preferably 0.005 to 0.0 45. The molar ratio of bromine-providing compound to oxidizing agent is from 0.4 to 36, preferably 1 to 20. In selecting suitable oxidizing agents and bromine-providing compounds, it is preferred to use those exhibiting activity at a pH of from 1 to 4 and a temperature of from 70° C. to 120° C.

While the mechanism of the isomerization reaction is not presently understood, it is believed that bromine-providing compounds suitable as catalysts will form a bromonian ion by reaction with the olefinic bond of maleic acid. The oxidizing agent supplies electrons to destabilize the bromonion ion and allow formation of fumaric acid. The formation of bromonion ion in the context of bromine addition to olefinic compounds is described at pages 348–350 of "Advanced Organic Chemistry," by E. Earl Royals, copyright 1954 by Prentice-Hall, Inc.

In keeping with the invention, it may be preferred to pass the fumaric-containing solution from the isomerization step over an anion exchange resin (step VIII) and activated carbon (step IX) to remove bromide ion and trace color bodies prior to recycle. The pH of the solution, about 3–4 after the isomerization step, rises to about 7 when the bromide ion is removed. These steps extend the service life of the solution, but are not required. Calgon's APC granular activated carbon and Rohm & Haas' MSA-1 anion exchange resin conveniently may be used. When these materials are employed as a packed bed, typical liquid hourly space velocities (that is, volume of solution per volume of bed per hour) may be from about 1.5 to about 2.5 for activated carbon and from about 2.3 to about 4.5 for anion exchange resin.

The pH of the fumaric acid-containing solution (step X) is raised to about 8 to 9 by addition of ammonium hydroxide (step XI) or another material which does not introduce ionic species which form undesirable by-products or interfere with the enzymatic reactions. During the isomerization reaction, fumaric acid may tend to precipitate. However, as the pH is raised the fumaric acid goes into solution. At a pH of 8 to 9 the aqueous solution has a fumaric acid concentration of about 0.4 to 1.6 molar. If necessary, the temperature is adjusted so that it is within the range of 10° C. to 50° C. The fumaric-containing solution, either direct from the isomerization step or after passage through activated carbon and/or anion exchange resin, then is passed into contact with the aspartase or aspartase-producing microorganisms (step I) to complete the recycle.

A divalent metal ion may be added to the enzymatic reaction solution (i.e., the substrate solution of step X) to enhance the enzymatic activity and stability of the immobilized microorganism, although it has been discovered that such enhancement of activity is frequently unnecessary for short periods of time. Suitable examples of the divalent metal ions which can be employed include calcium, magnesium, manganous and strontium ions. If employed, the concentration of divalent metal ion in the substrate solution is from 0.1 to 10 millimoles/liter.

Microorganisms which produce aspartase are employed for certain embodiments of the present invention. Examples of aspartase-producing microorganisms include appropriate strains of the following:

*Pseudomonas fluorescens*
*Serratia marcescens*
*Bacterium succinium*
*Bacillus subtilis*
*Aerobacter aerogenes*
*Micrococcus sp.*
*Escherichia coli.*

It should be noted that the present invention is not limited to the use of these specific microorganisms but includes within its scope the use of all aspartase-producing microorganisms. The identity of cultures of aspartase-producing microorganisms can readily be determined by consulting patents and journal references. For example, U.S. Pat. Nos. 3,791,926 and 3,198,712 both describe aspartase-producing organisms. In addition, it is contemplated that purified or synthetic aspartase may be used in the process of this invention.

Conventionally, microorganisms or enzymes are employed in the form of a liquid broth and the substrate (e.g., fumaric acid) is brought into contact with the broth. Following conversion, the product (e.g., aspartic acid) is separated from the cell mass, nutrients, water and other materials. These conventional steps can be employed in the process of the invention. However, it may be preferred to immobilize the microorganisms or enzyme in an inert carrier to facilitate separation from the product solution prior to pH adjustment and precipitation of the L-aspartic acid. In keeping with the invention, the reduction of pH and precipitation of L-aspartic acid can be accomplished by the addition of maleic acid to a variety of aspartic acid-containing solutions, regardless of origin.

The aspartase or aspartase-producing microorganisms can be immobilized in conventional polymer systems. The use of carrageenan is described by Sato in *Biochemica et Biophysica Acta*, 570, 179–186 (1979). Ethylene/maleic anhydride polymers are described in U.S. Pat. No. 3,649,457. Polyacrylates and polyacrylamides are described in U.S. Pat. Nos. 3,791,926 and 3,898,128, e.g., polymers formed from acrylamide, N,N'-lower alkylene-bis (acrylamide) and bis (acrylamidomethyl) ether. The journal article by Sato and U.S. Pat. Nos. 3,649,457; 3,791,926; and 3,898,128 are hereby incorporated by reference to the extent they describe the carrier systems mentioned above.

As examples of preferred carrier systems, the hydrophilic polyurethane polymers described in the co-pending applications discussed above may be utilized. These carrier systems may employ either polyether or polyester polyurethane foams. In one preferred embodiment, the carrier may be a hydrophilic polyether polyurethane foam wherein at least 50 mole % of the alkylene oxide units in the polyether segments of the polyurethane are ethylene oxide, said foam having, in this embodiment, an aspartase-producing microorganism immobilized therein.

The polyether segments of the foam of this embodiment preferably contain at least 90 mole % of ethylene oxide units. Depending upon the amount of crosslinking agent employed, the foam can be either rigid or flexible. Based on the dry weight of the microorganism employed, the weight ratio of the polyurethane polymer to microorganisms in the foam is from about 2:1 to 4:1. Prior to admixture of the culture with the prepolymer, the dry weight of microorganisms in the culture can be determined by evaporating the culture to dryness at a suitable temperature, e.g., 50° C. Thereafter on admixing a similar culture with the prepolymer, it has been found that from 50 to 90% of the microorganisms can be immobilized in the foam.

By the term "immobilization" it is meant that the microorganisms are retained in the foam rather than being leached therefrom upon contact with water or an aqueous substrate solution. It is believed that during the foaming process binding occurs between the isocyanate groups of the prepolymer and groups on the surface of the microorganisms, e.g., amino groups.

Urethane prepolymers useful in preparing the polyurethane foam are prepared by capping a polyoxyalkylene polyol with an excess of polyisocyanate, e.g., toluene diisocyanate. Prior to capping, the polyol should have a molecular weight of from about 200 to about 20,000 and preferably from about 600 to about 6,000. The hydroxyl functionality of the polyol and the corresponding isocyanate functionality following capping is from 2 to about 8. If foams are formed from prepolymers with an isocyanate functionality of about 2, the resulting product is essentially linear and does not have as much tensile strength as if it were crosslinked. Accordingly, a hydroxyl functionality greater than two per molecule is desired. This can be obtained by using mixtures of diols with triols or other higher functionality polyols, or triols or other higher order polyols themselves can be capped with di- or polyisocyanates.

Examples of suitable polyols (to be capped with polyisocyanates) include: (A) essentially linear polyols formed, for example, by reaction of ethylene oxide with ethylene glycol as an initiator. Mixtures of ethylene oxide with other alkylene oxides can be employed so long as the mole percent of ethylene oxide is at least 50 percent. Where the linear polyethers are mixtures of ethylene oxide with, e.g., propylene oxide, the polymer can be either random or a block copolymer and the terminal units can be either oxyethylene or oxypropylene.

A second class of polyol (B) includes those with a hydroxyl functionality of 3 or more. Such polyols are commonly formed by reacting alkylene oxides with a polyfunctional initiator such as trimethylolpropane, pentaerythritol, etc. In forming a polyol of class (B), the alkylene oxide used can be ethylene oxide or mixtures of ethylene oxide with other alkylene oxides.

Useful polyols can be further exemplified by (C) linear branched polyfunctional polyols as exemplified in (A) and (B) above, together with an initiator or crosslinker. A specific example of a polyol of class (C) is a mixture of polyethylene glycol (m.w. about 1,000) with trimethylolpropane, trimethylolethane or glycerine. This mixture subsequently can be reacted with excess polyisocyanate to provide a prepolymer useful in the invention. Alternatively, the linear or branched polyols (e.g., polyethylene glycol) can be reacted separately with excess polyisocyanate. The initiator, e.g., trimethylolpropane, also can be reacted separately with polyisocyanate. Subsequently, the two capped materials can be combined to form the prepolymer.

Suitable polyisocyanates and initiators are set forth in U.S. Pat. No. 3,903,232, incorporated herein by reference. The initiators are generally water-soluble or water-dispersible crosslinking agents as described in U.S. Pat. No. 3,903,232.

The foams for use with this embodiment of the present invention are prepared by admixing a culture of the aspartase-producing microorganisms directly with a urethane prepolymer in the presence of sufficient water to promote foaming. Conventionally, the water is carried in the culture, e.g., suitable cultures generally comprise from about 10 to 90 weight % of water. (The water content of the particular culture is determined by evaporating a sample of the culture to dryness as described above.) Due to the presence of water in the culture being admixed, the prepolymer will undergo foaming and the microorganisms simultaneously will be immobilized in the foam.

To optimize immobilization, the pH of the aqueous culture is from about 4 to about 11 and preferably is in excess of 7. During immobilization, the prepolymer/water weight ratio is generally from 2:1 to 1:2 and preferably from 3:2 to 2:3, said water being provided by the culture or by combination of the culture and water added prior to or during admixture. During mixing, the culture should be sufficiently dispersed in the prepolymer or prepolymer/water combination so that no visually discernible lumps are present. Following admixture, the foaming reaction generally is completed within 5-10 minutes and the foam is cured to its final rigid or flexible form in an additional 5-10 minutes. However, with large foam masses it is conceivable that the times for foam formation and curing can be considerably extended.

The method of this invention may be performed either on a batch or continuous basis. The concentration of substrate (i.e., fumarate ion) is described above. In a batch process, the immobilized microorganisms are contacted with the substrate and the mixture is incubated at a temperature of 30° C. to 40° C., with stirring, until the reaction is complete. When the reaction is completed, the foam (or other carrier) is separated and can be stored under refrigeration for subsequent use. L-aspartic acid is recovered from the substrate by addition of maleic acid, crystallization and centrifugation as described above. Isomerization of maleic acid to fumaric acid for re-use also is as described above.

Alternatively, the enzymatic reaction can be performed by a column method, i.e., on a continuous basis. For example, the immobilized microorganisms are packed into a column at a sufficient density to remain permeable to flow-through of the substrate. The substrate concentration is as described above. The substrate solution, having a pH of from 8 to 9 and comprising fumarate ion and ammonium ion, is passed through the column at a temperature of from about 10° C. to 50° C. (preferably 20° C. to 45° C.) and at a suitable flow rate. An aqueous solution containing L-aspartic acid is obtained as the column effluent.

This L-aspartic acid-containing effluent is then contacted with maleic acid according to the method of this invention. The precipitated L-aspartic acid may be isolated and further processed, as by water washing, for example. The maleic acid in the supernatant liquid may be isomerized as described above, the pH raised to about 8 to 9, and the resulting fumaric acid-containing solution recycled through the column for further L-aspartic acid production.

The following examples will demonstrate the method of this invention using *E. coli* cells immobilized in a flexible hydrophilic polyurethane foam. These examples are given for illustrative purposes only and are not meant to limit the invention described herein except as defined by the claims appended hereto.

PREPARATION OF PREPOLYMER A

Prepolymer A was prepared by admixing two molar equivalents of polyethylene glycol having an average molecular weight of 1,000 (PEG - 1,000) and one molar equivalent of trimethylolpropane (TMOP). The admixture was dried at 100°-110° C. under a pressure of 5-15 Torr to remove water. The resulting dried mixture was slowly added over a period of about one hour to a vessel containing 6.65 molar equivalents of toluene diisocyanate (TDI) while stirring the TDI and polyol mixture. The temperature was maintained at 60° C. with stirring for three additional hours.

PREPARATION OF FOAM, SUBSTRATE MEDIA AND COLUMN

*E. coli* cells (ATCC 11,303) suspended in 0.1M phosphate buffer (pH 8.0) were spun down at 16,000 rpm for five minutes. The cell mass was placed under refrigeration and drained overnight. The cells (200 gms) were admixed with 200 gms of Prepolymer A. Due to the water in the cell mass, a flexible hydrophilic polyurethane foam was formed which cured in about five minutes. The cells were encapsulated within and/or bound to the polyurethane foam matrix. The cured foam was cut into particles of approximately 2.5 mm × 2.5 mm.

A substrate media was prepared as follows: 348 gm fumaric acid and 530 mg $MgCl_2.6H_2O$, dissolved in 25% ammonium hydroxide with pH adjustment to 8.5 with concentrated ammonium hydroxide. Sufficient deionized water was added to bring the volume to 2000 cc. The temperature of the substrate was maintained at 37° C.

The foam particles were packed into a 200 cc column equipped with a water jacket. The bed volume was about 180 $cm^3$. The height of the bed was about 28 cm.

EXAMPLE 1

Substrate solution was passed through the column described above at a flow rate of about 25 ml/mm. A two-liter sample of the aqueous substrate solution emanating from the column had an L-aspartic acid concentration of about 1.5 molar and a pH of about 8.5. The pH was reduced to 3.5 by addition of 350 grams (3 moles) of maleic acid solution derived from a maleic anhydride melt hydrolyzed with water. The mixture of L-aspartic and maleic acids was warmed to about 60° C. and was then allowed to cool to precipitate crystals of L-aspartic acid. The crystals were washed with deionized water and dried. Crystal analysis showed 98.8% aspartic acid, 0.4% maleic acid, and a small amount of fumaric acid. The supernatant liquid from the crystallization and the wash water were combined. The pH of this mixture was 3.5.

To accomplish isomerization of the maleic acid in the mother liquor separated from the L-aspartic acid crystals, 0.45 weight percent solid ammonium bromide and 2.7 weight percent solid ammonium persulfate were added. The weight percent is based on the weight of the maleic acid. Thereafter, the solution was heated with agitation to approximately 74°-80° C. for about 30 minutes. Considerable amounts of solid fumaric acid precipitated from solution. After cooling, the pH of the entire mixture (which was about 3.5) was raised to 8.5 by addition of ammonium hydroxide which resulted in solution of the fumaric acid. This isomerization mixture was about 1.1 molar with respect to fumaric acid and about 0.4 molar with respect to maleic acid.

The mixture was passed through the column described above (solution temperature about 37° C.) at a flow rate of about 25 ml/min. The concentration of L-aspartic acid in the effluent from the column was about 1.08M; the concentration of fumaric acid was about 0.02M. The concentration of maleic acid remained at about 0.4M, indicating that the maleic acid was an inert material.

In the isomerization step, the isomerization (maleic-to-fumaric) was about 74%. If the procedure is varied to lower the pH to about 1.5 with sulphuric acid, the isomerization is about 95% complete. However, this introduces relatively large amounts of ammonium sulphate into the system which creates undesirable waste disposal problems.

EXAMPLE 2

The procedure of Example 1 was repeated except that following isomerization and adjustment of the pH to 8.5, an anion exchange column manufactured by the Dow Chemical Company (Dowex MSA-1), was utilized to remove bromide ion. The solution was also passed through a column of activated carbon to remove color bodies. Thereafter, the solution was passed through the microbiological column described above (temperature 37° C.; flow rate 25 ml/min; run time 2 hrs.), resulting in an L-aspartic acid concentration of 1.2M; and maleic acid concentration of 0.3M. The concentration of maleic acid was not affected appreciably by contact with the column, i.e., the maleic acid appeared to be inert. The percent conversion (on a molar basis) of fumaric to L-aspartic acid was about 80%.

Alternatively, following isomerization the pH may be adjusted to about 8 with ammonium hydroxide. The solution then would be passed through the ion exchange column, where the pH would be increased further to about 8.5.

EXAMPLE 3

Solutions were passed through the column (according to the method of Example 1) wherein the fumaric acid concentration was about one molar and the concentration of maleic acid was about 0.5 molar. The conversion rates were similar to those described above and the maleic acid appeared to be inert, i.e., the maleic acid was not converted into other materials and did not appear to affect the enzymatic activity of the microorganisms.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing L-aspartic acid wherein a substrate comprising fumarate ion is contacted with aspartase or aspartase-producing microorganisms immobilized in an inert carrier to convert fumarate ion to L-aspartate, the improvement comprising: reducing the pH of the aqueous solution resulting from contact with said aspartase or aspartase-producing microorganisms to about 3 to 4 by addition of maleic anhydride, maleic acid or salts thereof to insolubilize L-aspartic acid while providing maleic acid in the supernatant phase, removing the insolubilized L-aspartic acid, isomerizing the maleic acid in the supernatant phase to fumaric acid, adjusting the pH of the supernatant phase to about 8 to 9, and passing the supernatant phase into contact with the aspartase or aspartase-producing microorganisms.

2. An improved process as in claim 1 wherein the solution contacted with the aspartase or aspartase-producing microorganisms possesses a pH of from about 8 to about 8.5.

3. An improved process as in claim 1 wherein the solution contacted with the aspartase or aspartase-producing microorganisms has from about 0.1 to 10.0 millimoles per liter of a water-soluble divalent metal ion dissolved therein.

4. An improved process as in claim 1 wherein the isomerization step is carried out catalytically at a pH of from about 3 to 4.

5. An improved process as in claim 1 wherein the isomerization step is carried out catalytically utilizing a material recognized as possessing the capability to form bromonion ions.

6. An improved process as in claim 1 wherein the aspartase or aspartase-producing microorganisms are immobilized in a synthetic polymer foam.

7. An improved process as in claim 6 wherein the foam is a hydrophilic polyurethane.

* * * * *